United States Patent [19]

Davies

[11] Patent Number: 4,492,617

[45] Date of Patent: Jan. 8, 1985

[54] METHOD OF PREPARING TETRAHALOBENZENE COMPOUNDS

[75] Inventor: Gwilym R. Davies, Kingsley, England

[73] Assignee: Imperial Chemical Industries PLC, London, England

[21] Appl. No.: 569,898

[22] Filed: Jan. 11, 1984

[30] Foreign Application Priority Data

Nov. 10, 1983 [GB] United Kingdom ............... 8329956

[51] Int. Cl.$^3$ .................................................. C25B 3/00
[52] U.S. Cl. ................................ 204/73 R; 204/59 R
[58] Field of Search ........................... 204/59 R, 73 R

[56] References Cited

PUBLICATIONS

Ross et al., *J. Am. Chem. Soc.* 92:20, Oct. 7, 1970, pp. 6003–6006.
Chemical Abstracts 67 (12): 55214m.
Beltzley and Russell, JACS 72 382 (1950).
Aeberli et al., J. Org. Chem. 40 382 (1975).
Chemical Abstracts 93 (6): 47238u.
Chemical Abstracts 89 (5): 42750n.
Chemical Abstracts 83 (1): 9993x.

*Primary Examiner*—John F. Niebling
*Attorney, Agent, or Firm*—Cushman, Darby & Cushman

[57] ABSTRACT

Tetrahalobenzene compounds of the formula (IX):

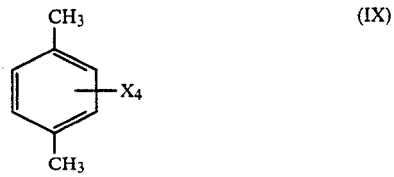

in which each X is independently chloro or fluoro, are prepared by electrolyzing in a protic medium a compound of the formula (IV):

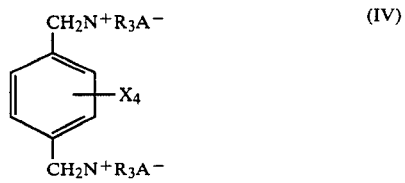

in which X has the meaning already given, each R is independently $C_{1-4}$ alkyl and A is a radical capable of forming an anion $A^-$.

The compounds are useful in the synthesis of insecticides.

3 Claims, No Drawings

METHOD OF PREPARING TETRAHALOBENZENE COMPOUNDS

This invention relates to a method of preparing tetrahalobenzene compounds useful in the synthesis of insecticides.

According to the present invention there is provided a method of preparing tetrahalobenzene compounds of the formula (I):

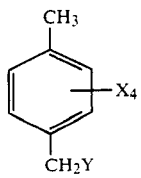

in which each X is independently chloro or, preferably, fluoro and Y is hydrogen or $-N^+R_3A^-$ in which each R is independently $C_{1-4}$ alkyl, especially methyl or ethyl, and A is a radical capable of forming an anion $A^-$, the method comprising the steps of
(a) alkylating a compound of formula (II):

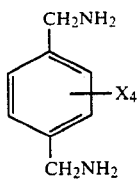

or a salt thereof, to form a compound of formula (III):

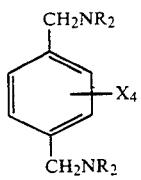

(b) treating the compound of formula (III) with a quaternizing agent of formula RA to form a compound of formula (IV):

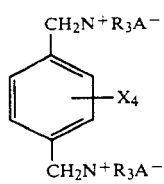

in which X and A have the meanings hereinbefore defined;
and
(c) partially or completely reductively cleaving the compound of formula (IV) to replace one or both $-N^+R_3A^-$ groups by hydrogen.

The invention also includes the process steps (a), (b) and (c) individually and the combinations of steps (a) and (b) and (b) and (c), the intermediate compounds of the formulae (III) and (IV) and compounds of the formula (I) in which Y is $-N^+R_3A^-$.

Step (a) of the process may be carried out by any of the methods well known in the chemical art for the preparation of tertiary amines from primary amines, for example, by either (a)(i) treating the compound of formula (II) with one or more alkylating agents containing the R radicals; or
(a)(ii) reductively alkylating the compound of formula (II) or a salt thereof with one or more aldehydes or ketones or a mixture of both in the presence of a reducing agent, the R radicals being formed by the reduction of the aldehyde or ketone and amine reaction products.

In step (a)(i), the compound of formula (II) may be treated with, typically, one or more alkyl halides in an alcoholic solution. The reaction mixture is made alkaline and the tertiary amine recovered, by, for example, distillation. Conveniently, when the R radicals are to be the same, a single alkylating agent may be used in slight excess of the stoichiometric amount required to form the di-tertiary amine. However, it is also envisaged that different alkylating agents could be used, either in admixture or separately, to form a range of products having different combinations of alkyl groups attached to the nitrogen atoms of compound (III).

In alternative step (a)(ii), the compound of formula (II) or a salt thereof may be reacted with one or more aldehydes or ketones or mixtures thereof in the presence of, for example, hydrogen and a hydrogenation catalyst, such as palladium on carbon, at temperatures preferably above 45° C. to avoid too slow a reaction. Conveniently, when the R radicals are to be the same, a single aldehyde or ketone is used in slight excess of the stoichiometric amount required to form the di-tertiary amine. However, it is also envisaged, although not preferred, that step (a)(ii) could proceed in stages using in each stage different aldehydes or ketones or mixtures thereof to provide different values of R.

Step (b), the quaternisation of the compound of formula (III), may be carried out by any of the methods well known in the chemical art for forming quaternary compounds. Conveniently, the compound of formula (III) is treated with an appropriate alkyl halide or sulphate, e.g. dimethylsulphate, in an alcoholic solution and, as necessary, in the presence of an acid binding agent such as magnesium oxide. The acid binding agent is used to mop up any acid formed as a result of hydrolysis of the quaternising agent.

In a preferred aspect of the process of the invention, 1,4-bis(aminomethyl)-2,3,5,6-tetrafluorobenzene or a salt thereof is tetramethylated by step (a)(ii) in a single stage using formaldehyde as the aldehyde, and quaternised with a methyl halide.

The intermediate compound having the formula (V):

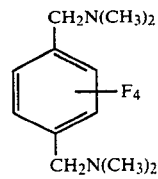

and the diquaternary salt obtained therefrom, having the formula (VI):

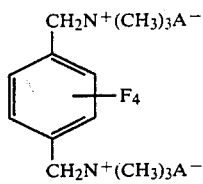

(VI)

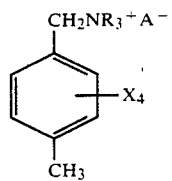

(VII)

in which A⁻ has the meaning hereinbefore defined, are preferred compounds of the invention.

In step (c), the di-quaternary compound (IV) is partially or completely cleaved, that is deamminated, to form either the monoquaternary derivative, i.e. compound (I) in which Y is $-N^+R_3A^-$, or the dimethyltetrahalobenzene, i.e. compound (I) in which Y is H. Deammination is achieved with a reducing agent such as hydrogen in the presence of a suitable catalyst. The most suitble catalyst is palladium, especially palladium on carbon, preferably having a metal loading of from 3 to 20% by weight of palladium on carbon and especially 5% and 10% palladium on carbon which are grades of catalyst commercially available. Catalyst usages will depend on the temperature and pressure of reduction and whether complete or partial deammination is desired. These factors are more fully discussed later. In general, however, catalyst usages will range from 1.25% for partial deammination to 5% by weight of metal in the catalyst on diquaternary compound (IV) for complete deammination, when reduction is carried out at elevated temperatures and pressures, and up to 10% when complete deammination is carried out at atmospheric pressure.

In a preferred method of complete deammination to form the dimethyltetrahalobenzene, the diquaternary compound (IV) is electrolysed in a protic medium, preferably water.

Suitable materials for use as the cathode in this electrolytic method are lead, mercury and amalgamated metals such as amalgamated lead. The anode is conveniently platinum. Reduction takes place at potentials more negative than $-1.0$ V against a saturated calomel electrode.

Electrolysis is preferably carried out in a divided cell, for example, an H-cell or Filter Press (Plate-and-Frame) cell having a diaphragm which is suitably a cation exchange membrane, for instance a Nafion membrane. The diquaternary compound in the protic medium is used as the catholyte. When water is the protic medium, the concentration of diquaternary salt in the aqueous solution is preferably from 7.5% w/v up to a saturated solution, ideally about 20% w/v. The anolyte may be any suitable electrolyte, usually a salt solution such as a saturated aqueous solution of sodium sulphate. The voltage applied across the electrodes will normally be sufficient to give a current density of, typically, about 100 mAcm$^{-2}$, deammination being completed in about 5 hours at ambient temperature. During the electrolysis, a portion of the 1,4-dimethyltetrahalobenzene separates from the aqueous trialkylamine, which is formed as a result of deammination, a portion dissolves in the aqueous solution and a portion sublimes onto the wall of the electrolytic cell. The portions are dissolved in ether and residual trialkylamine washed out of the ether with aqueous inorganic acid. The crude 1,4-dimethyltetrahalobenzene may be purified by distillation.

The monoquaternary salt having the formula (VII):

in which X, R and A have the meanings hereinbefore defined, may be obtained by terminating the deammination step (c) partway through. This is most conveniently done when hydrogen is used as the deamminating agent in the presence of a catalyst. Under pressures up to about 17 atmospheres, particularly in the range of from 3 to 17 atmospheres, temperatures in the range of from 70° to 120° C., particularly 75° to 85° C. and using a 5% palladium on carbon catalyst, the monoquaternary salt can be obtained. At lower pressures and/or temperatures, higher catalyst usages and/or metal loadings, e.g. 10% palladium on carbon, and extended reaction times are needed. At higher temperatures and/or pressures and/or catalyst usages deammination proceeds further and the 1,4-dimethyltetrahalobenzene is formed.

Whether the diquaternary compound (IV) is deamminated by a chemical or electrochemical reduction, there is no substantial loss of the ring fluorine atoms. In contrast, attempts to deaminate the diamine (II) and the tetra-alkylated compound (III) by catalytic hydrogenolysis using palladium catalysts have resulted in total and partial loss, respectively, of the ring halogen atoms.

The starting material, the diamine (II), may be obtained by a process which comprises reacting the appropriate 1,4-dicyanotetrahalobenzene with hydrogen in the presence of a hydrogenation catalyst under acid conditions, as described in UK patent application No. 8312493 (Publication No. 2120666). Conveniently, this process may be combind with step (a)(ii) of the present process without isolation of the compound (II). Thus, for instance, the 1,4-dicyanotetrahalobenzene may be reacted with hydrogen in a pressurised autoclave at an elevated temperature in the presence of a hydrogenation catalyst, e.g. 5% palladium on carbon, an inert solvent, suitably methanol, an acid, preferably sulphuric acid and, optionally, a small amount of water. When hydrogenation is judged complete, an appropriate quantity of aldehyde or ketone or mixture thereof may be introduced to the autoclave and reacted with the hydrogenation product to form the compound of formula (III). Alternatively, the process for preparing the 1,4-diaminomethyltetrahalobenzene and step (a)(ii) may be combined in a single stage, the aldehyde or ketone or mixture thereof being introduced to the autoclave before hydrogenation is commenced. In this case it is desirable to exclude water from the autoclave.

If the 4-methyl-2,3,5,6-tetrahalobenzyl ester of a carboxylic acid is desired, then rather than proceeding via the 1,4-dimethyltetrahalobenzene and the appropriate alcohol or halide the ester may be formed by direct reaction of the monoquaternary salt (VII) with the carboxylic acid or a reactive derivative thereof, such as an alkali metal salt, an ammonium salt or an alkylammonium salt, preferably in a suitable organic solvent.

1,4-Dicyanotetrafluorobenzene may be obtained by fluorinating the corresponding tetrachlorinated compound with potassium fluoride in a polar aprotic solvent. 1,4-Dicyanotetrachlorobenzene is, itself, obtained from the commercially available tetrachloroterephthaloyl chloride by treatment with aqueous ammonia to give the diamide followed by dehydration using phosphorus oxychloride.

The invention is illustrated by the following Examples 1 to 12 in which percentages are by weight. Example 13 is included for comparative purposes only.

Preparation of
1,4-bis(dimethylaminomethyl)-2,3,5,6-tetrafluorobenzene

EXAMPLE 1

2 g of 1,4-bis(aminomethyl)-2,3,5,6-tetrafluorobenzene disulphate, 25 ml methanol, 25 ml water, 3 ml of 37% aqueous formaldehyde and 0.5 g 5% palladium on carbon catalyst were charged to a 100 ml flask fitted with a stirrer, an inlet connected to a supply of hydrogen and a gas outlet. The mixture was agitated while passing hydrogen through at 50 ml/min. After 3 days the mixture was added to strong sodium hydroxide solution. An ether extract was shown by gas liquid chromatography to contain none of the original diamine, but a substantial quantity of the N,N,N',N'-tetramethyl derivative, contaminated with about 1–2% of the corresponding N,N-dimethyl compound.

EXAMPLE 2

5 g of 1,4-dicyano-2,3,5,6-tetrafluorobenzene, 0.25 g of 5% palladium on carbon, 2 ml water, 70 ml methanol and 3.0 g sulphuric acid, were loaded to a glass-lined rotating autoclave which, after purging, was pressurised to 15 atmospheres with hydrogen. The autoclave was rotated for 6 hours at 75° C. (maximum autogeneous pressure, 17 atmospheres). The autoclave was cooled, vented, and, after 15 ml of 37% formaldehyde solution was added, pressurised again to 15 atmospheres and rotated for 6 hours at 75° C. The reaction solution was filtered and the filtrate reduced in volume by evaporation at 50° C. at 6 cms Hg pressure. 5.8 g of crude 1,4-bis(dimethylaminomethyl)-2,3,5,6-tetrafluorobenzene was isolated by evaporating ether extracts of a strongly alkaline solution of the residue.

EXAMPLE 3

5.0 g of 1,4-dicyano-2,3,5,6-tetrafluorobenzene, 70 ml of methanol, 5 ml of water, 3.5 g of sulphuric acid and 0.125 g 5% palladium on carbon (T37 dry powder obtained from Johnson Matthey Chemicals Ltd.) were loaded into a glass-lined rotating autoclave and hydrogenated for 6 hours at 13° C. and 30 atomspheres. 15 ml of 37% formalin solution were added and the mixture treated with hydrogen for 6 hours at 60° C. and 20 atmospheres. The product solution was filtered and methanol removed from the filtrate using a vacuum rotary evaporator. 70° Tw caustic soda solution was added dropwise, and the precipitate (5.6 g) isolated. The isolated material (5.03 g) was recrystallised from 5 ml of toluene giving 3.0 g white solid having a melting point of 73.5° C.

Elemental analysis of the solid gave C 54.2%, H 6.4%, N 10.6%, F 29.2% against theory for 1,4-bis(-dimethylaminomethyl)-2,3,5,6-tetrafluorobenzene of C 54.5%, H 6.1%, N 10.6%, F 28.6%. Analysis by nmr gave delta=2.19 (6p,s) and delta=3.60 (2p,s) attributable to $(CH_3)_2$—N—C— and Ar—$CH_2$—N protons, respectively. Analysis by UV (0.5N HCl in 50/50 methanol/water) gave $\pi$max=279 nm, $\epsilon = 2.17 \times 10^3$, $\lambda$min=237 nm. The Infra Red spectrum of the solid (KBr disc) showed peaks at the following wavelengths: 2985, 2975, 2860, 2820, 2780, 2760, 1485, 1465, 1440, 1415, 1405, 1375, 1318, 1277, 1255, 1177, 1154, 1096, 1030, 940, 873, 840, 700, 601 cm$^{-1}$.

EXAMPLE 4

5 g of 1,4-dicyano-2,3,5,6-tetrafluorobenzene, 0.5 g of 5% palladium on carbon, 3.5 g of sulphuric acid, 75 ml of methanol and 5 g formaldehyde were loaded to a glass-lined rotating autoclave, and, after purging, pressurised to 20 atmospheres with hydrogen. The autoclave was rotated at 75° C. for 12 hours. 6.08 g crude material were isolated by the procedures described in Example 2, and consisted of 89.7% 1,4-bis(dimethylaminomethyl)-2,3,5,6-tetrafluorobenzene (82.6% yield).

Quaternisation of
1,4-bis(dimethylaminomethyl)-2,3,5,6-tetrafluorobenzene

EXAMPLE 5

2.0 g of crude 1,4-bis(dimethylaminomethyl)-2,3,5,6-tetrafluorobenzene, 60 ml 80% ethanol and 1.6 g methyl chloride were heated to 40° C. for 23 hours in a flask fitted with a reflux condenser topped with a "Dri-Cold" finger. Further methyl chloride was added and the mixture heated for another 24 hours. Only trace quantities of the starting tertiary amine remained.

EXAMPLE 6

2.0 g of crude 1,4-bis(dimethylaminomethyl)-2,3,5,6-tetrafluorobenzene (81% pure), 50 ml 75% aqueous ethanol and 0.3 g magnesium oxide were heated to 55° C. and a stream of methyl chloride passed through for 24 hours. The suspension was filtered, and the solvent removed from the filtrate to give 2.5 g of the crude diquaternary compound. Potentiometric titration gave a titre equivalent to about 1.5% of the original diamine.

EXAMPLE 7

100 g of 1,4-bis(dimethylaminomethyl)-2,3,5,6-tetrafluorobenzene (average strength 96.2%), 300 ml 74 OP ethanol and 200 ml water, were heated with methyl chloride at 68°-75° C. until analysis indicated less than 2.5% half-quaternised material to be present in the reaction mixture. The product solution was reduced to about 180 ml and separated solid was recrystallised from 100 ml of 50% aqueous ethanol to give 20.2 g of white solid.

Elemental analysis of the white solid, which was stable to at least 300° C., gave C 45.8%, H 6.1%, N 7.6%, Cl 19.5%, F 22.5% against theory for 1,4-bis(-trimethylammoniomethyl)-2,3,5,6-tetrafluorobenzene dichloride of C 46.0%, H 6.0%, N 7.7%, Cl 19.5% and F 20.8%. Analysis by nmr gave delta=3.32 (9p,s) and delta=4.87 (2 p,s) attributable to $N(CH_3)_3$ and Ar—$CH_2$—N, protons respectively. UV $\lambda$max=283 nm. The Infra Red spectrum of the solid (KBr disc) showed peaks at the following wavelengths: 3100, 2960, 1500, 1490, 1450, 1420, 1390, 1355, 1290, 1145, 1050, 985, 960, 900, 865, 695, 600 cm$^{-1}$.

Complete deammination of
1,4-bis(trimethylammoniomethyl)-2,3,5,6-tetrafluorobenzene dichloride (i) By hydrogenolysis

EXAMPLE 8

25 ml of the product solution obtained from Example 5 and 0.5 g of 5% palladium on charcoal powder, were charged to a glass-lined rotating autoclave, pressurised to 25 atmospheres with hydrogen, and rotated at 90° C. for 10 hours. 19 ml of solution containing 0.21 g 1,4-dimethyl-2,3,5,6-tetrafluorobenzene were recovered, with no defluorination indicated in any of the products when examined by GLC/mass spectroscopy.

(ii) By reductive electrolysis

EXAMPLE 9 (H Cell)

A solution of 1,4-bis(trimethylammoniomethyl)-2,3,5,6-tetrafluorobenzene dichloride (1.5 g) in 7.5 ml of water was introduced into the cathode compartment of an H cell of all-glass construction. A saturated aqueous solution of sodium sulphate (25 ml) was used as the anolyte. The H cell had a lead cathode (2 cm$^2$), a platinum on titanium anode and was divided by a Nafion membrane. A voltage of 11 v was applied across the electrodes for 2.6 hours at ambient temperature generating a current density of 100 mAcm$^{-2}$.

1,4-Dimethyl-2,3,5,6-tetrafluorobenzene separated from the catholyte giving a yield of 78%. The current efficiency was 65.5%.

EXAMPLE 10 (Filter Press cell)

A solution of 1,4-bis(trimethylammoniomethyl)-2,3,5,6-tetrafluorobenzene dichloride (20 g) in 100 ml water was used as the catholyte and a saturated aqueous solution of sodium sulphate (250 ml) as the anolyte in a Filter Press (Plate-and-Frame) divided cell. The cell had a lead cathode (30 cm$^2$), a platinum anode (30 cm$^2$) and a separating Nafion cation exchange membrane. A voltage of 8 v was applied across the electrodes for 2.3 hours at ambient temperature generating a current density of 100 mAcm$^{-2}$.

Conversion of the bis quaternary salt to 1,4-dimethyl-2,3,5,6-tetrafluorobenzene was 76% and the current efficiency was 66%.

Partial deammination of
1,4-bis(trimethylammoniomethyl)-2,3,5,6-tetrafluorobenzene dichloride

EXAMPLE 11

1.0 g of the diquaternary compound obtained from Example 6, 25 ml 75 % aqueous ethanol, and 0.5 g of 5% palladium on carbon were stirred under hydrogen at 70° C. for 43 hours. Only a trace quantity of 1,4-dimethyltetrafluorobenzene was formed. Potentiometric titration indicated formation of an amount of trimethylamine consistent with deammination to (4-methyl-2,3,5,6-tetrafluorobenzyl)-trimethylammonium chloride. Ultraviolet spectroscopy showed formation of a compound with λmax=273 nm [cf λmax=283 nm for the diquaternary compound (solvent 0.5N HCl in 50% aqueous methanol)].

EXAMPLE 12

6 g of 1,4-bis(trimethylammoniomethyl)-2,3,5,6-tetrafluorobenzene dichloride, 50 ml of ethanol, 7.5 ml of water and 1.5 g of 5% palladium on carbon (T87P dry powder obtained from Johnson Matthey Ltd.) were charged to a glass-lined rotating autoclave which was pressurised to about 6 atmospheres with hydrogen and rotated at 100° C. for 15 hours. The reaction mixture was filtered and solvent removed from the filtrate by evaporation to yield 5.9 g of solid material. This was extracted with 40 ml of acetone and the extract evaporated to give 7.7 g of a mixture of trimethylamine hydrochloride and a product identified in the mixture as (4-methyl-2,3,5,6-tetrafluorobenzyl)trimethylammonium chloride by proton nmr which gave delta=2.36 (3 p,poorly resolved triplet), delta=3.28 (9p,singlet), delta=−4.87 (2p,singlet), attributed to the CH$_3$—, —N(CH$_3$)$_3$+, and —CH$_2$—N protons respectively; UV λmax was 273 nm. Strength by nmr of the monoquaternary salt of the mixture was 69.4%.

EXAMPLE 13 (FOR COMPARATIVE PURPOSES ONLY)

Deamination of
1,4-bis(dimethylaminomethyl)-2,3,5,6-tetrafluorobenzene 1.0 g of crude 1,4-bis(dimethylaminomethyl)-2,3,5,6-tetrafluorobenzene, 30 ml of 90% ethanol, and 1.0 g of 5% palladium on charcoal were heated under hydrogen at atmospheric pressure at 50° C. for 19 hours, with agitation. Approximately 98% of the starting material was converted, mainly to p-xylene, monofluoro-p-xylene, and N-dimethyl-p-methylbenzylamines containing 1 to 3 nuclear fluorine atoms.

I claim:
1. Method of preparing tetrahalobenzene compounds of the formula (IX):

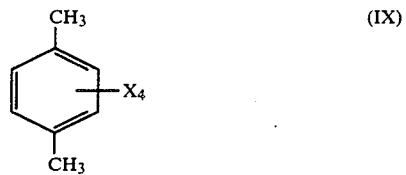

in which each X is independently chloro or fluoro, which comprises electrolysing in a protic medium a compound of the formula (IV):

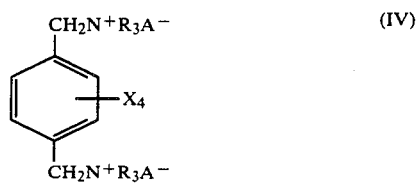

in which X has the meaning already given, each R is independently C$_{1-4}$ alkyl and A is a radical capable of forming an anion A$^-$.

2. A method according to claim 1 in which the protic medium is water.

3. A method according to claim 2 in which the concentration of compound (IV) in the water is from 7.5% w/v up to a saturated solution.

* * * * *